US008844358B2

(12) United States Patent
Chalupper et al.

(10) Patent No.: US 8,844,358 B2
(45) Date of Patent: Sep. 30, 2014

(54) HEARING-TEST METHOD

(75) Inventors: Josef Chalupper, Paunzhausen (DE); Beate Anna Maria Krämer, Fürth (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 715 days.

(21) Appl. No.: 13/043,743

(22) Filed: Mar. 9, 2011

(65) Prior Publication Data
US 2011/0219879 A1 Sep. 15, 2011

(30) Foreign Application Priority Data
Mar. 9, 2010 (DE) .......... 10 2010 010 764

(51) Int. Cl.
*A61B 5/12* (2006.01)
*H04R 25/00* (2006.01)

(52) U.S. Cl.
CPC *A61B 5/12* (2013.01); *H04R 25/70* (2013.01); *H04R 2225/55* (2013.01)
USPC .......................................... 73/585; 600/559

(58) Field of Classification Search
USPC .......................................... 73/585; 600/559
See application file for complete search history.

(56) References Cited

U.S. PATENT DOCUMENTS

| 5,143,081 | A * | 9/1992 | Young et al. | 600/554 |
|---|---|---|---|---|
| 2003/0078515 | A1* | 4/2003 | Menzel et al. | 600/559 |
| 2003/0083591 | A1* | 5/2003 | Edwards et al. | 600/559 |
| 2004/0049125 | A1 | 3/2004 | Nakamura | |
| 2004/0068200 | A1* | 4/2004 | Harrison et al. | 600/559 |
| 2004/0097826 | A1 | 5/2004 | Harrison et al. | |
| 2005/0192515 | A1* | 9/2005 | Givens et al. | 600/559 |
| 2007/0189545 | A1 | 8/2007 | Geiger et al. | |

FOREIGN PATENT DOCUMENTS

EP 1 813 190 A1 8/2007

OTHER PUBLICATIONS

Lorenzi, et al., "Speech perception problems of the hearing impaired reflect inability to use temporal fine structure", Proceedings of the National Academy of Sciences of the United States of America, Dec. 5 2006, pp. 18866-18869, vol. 103, No. 49.
Boretzki M. et al; "The Benefits of Nonlinear Frequency Compression for People with Mild Hearing Loss"; Internet Citation; pp. 1-7; 2009; Nov. 23, 2009.
Miller G. A. et al; "The Intelligibility of Interrupted Speech"; Journal of the Acoustical Society of America; vol. 22; No. 2; pp. 167-173; 1950.
Verschuure J. et al; "Intelligibility of Interrupted Meaningful and Nonsense Speech with and without Intervening Noise"; Perception &Psychophysics; vol. 33; No. 3; pp. 232-240; 1983; NL; Mar. 4, 1983.

(Continued)

*Primary Examiner* — Peter Macchiarolo
*Assistant Examiner* — Rose M Miller
(74) *Attorney, Agent, or Firm* — Laurence A. Greenberg; Werner H. Stemer; Ralph E. Locher

(57) ABSTRACT

The usefulness and sensitivity of a hearing-test method that can be performed over the Internet should be improved. To this end, it is proposed that meaningless syllables, so-called logatomes, are presented to a test person in fluctuating interference noise. Hence, the test can be offered internationally without change and there is no need to calibrate a computer used by the test person.

5 Claims, 2 Drawing Sheets

(56) References Cited

OTHER PUBLICATIONS

Stecker et al., "Perceptual training improves syllable identification in new and experienced hearing aid users" Journal of Rehabilitation Research and Development 2006 Rehabilitation Research and Development Service USA, vol. 43, No. 4, 2006, pp. 537-551, XP002630692.

Fullgrabe et al., "Making release for consonant features in temporally fluctuating background noise", Hearing Research, Elsevier Science Publishers, Amsterdam, NL, vol. 211, No. 1-2, Jan. 1, 2006, pp. 74-84, XP025083407.

Rickets et al., "Comparison of performance across three directional hearing aids", Journal of the American Academy of Audiology Apr. 1999 LNKD-PUBMED:10941709, vol. 10, No. 4, Apr. 1999, pp. 180-189, XP002630693.

* cited by examiner

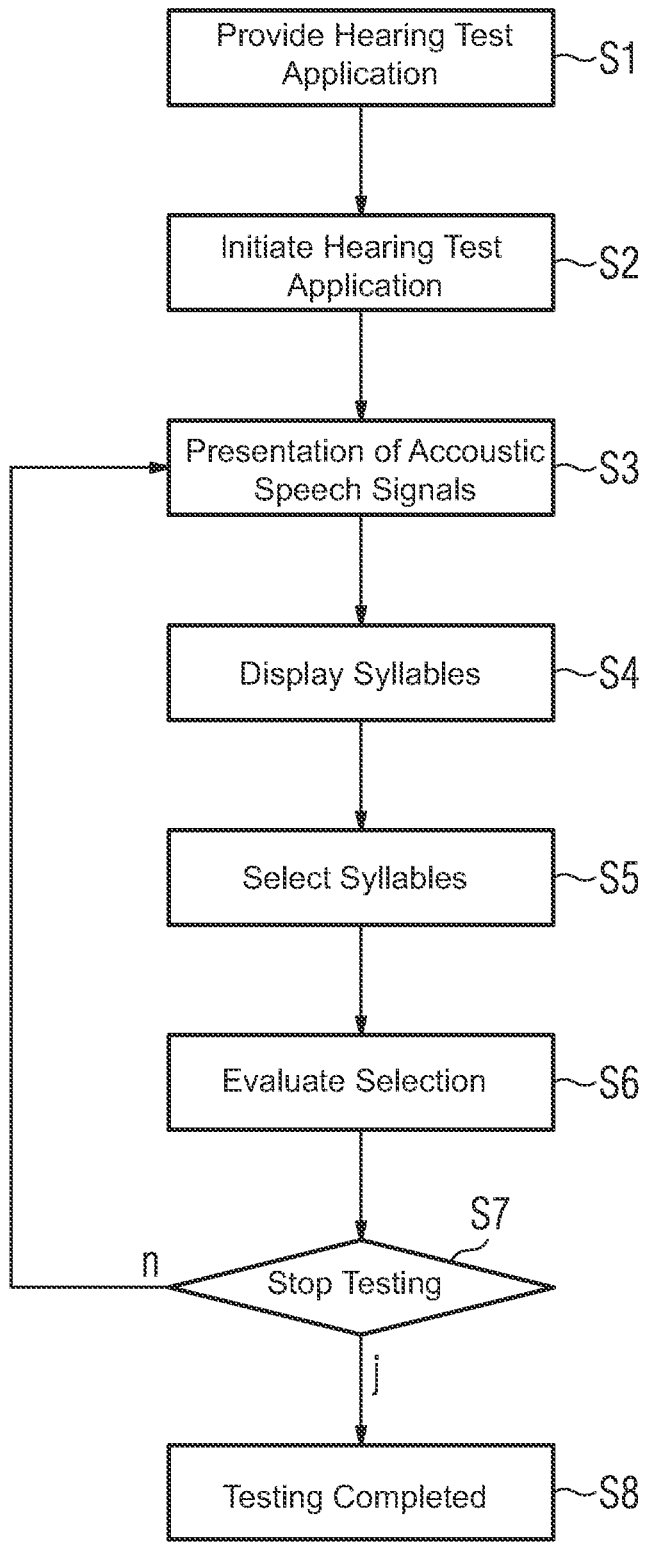

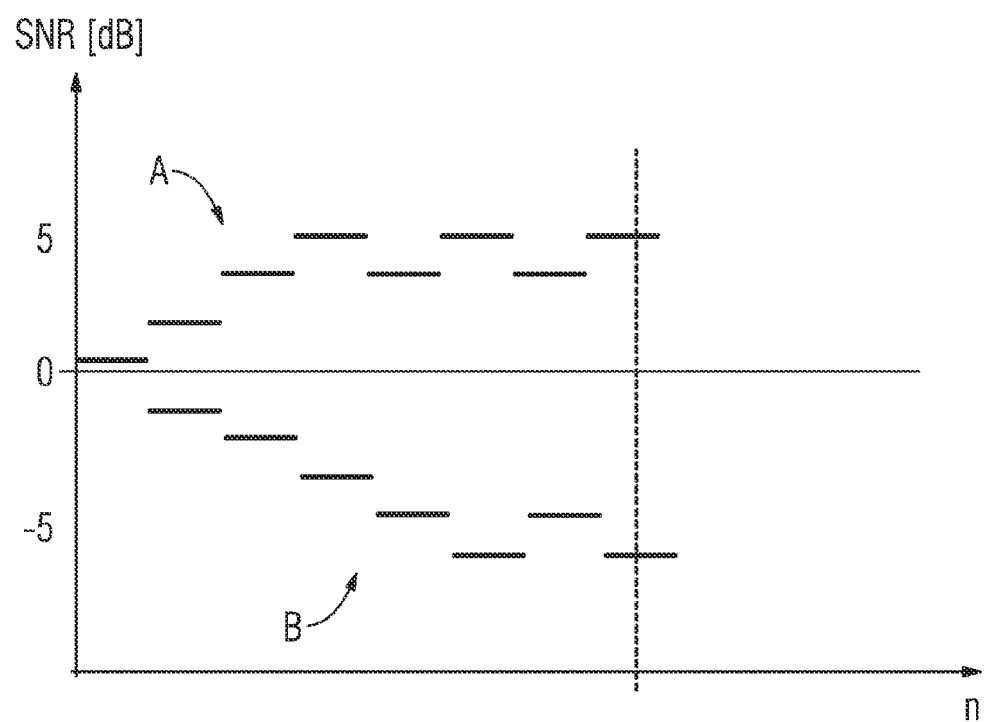

HEARING-TEST METHOD

CROSS-REFERENCE TO RELATED APPLICATION

This application claims the priority, under 35 U.S.C. §119, of German application DE 10 2010 010 764.6, filed Mar. 9, 2010; the prior application is herewith incorporated by reference in its entirety.

BACKGROUND OF THE INVENTION

Field of the Invention

A multiplicity of hearing-test methods are known for testing the hearing of a person (test person). In a hearing test that can be implemented easily, the person is presented with a tone at a particular frequency, very quietly at first and with increasing volume over time. The person signals as soon as they can perceive the tone, for example by actuating a switch. This test is repeated for various frequencies in the audible frequency range, and so a statement can be made as to whether, compared to someone with normal hearing, the person suffers from a loss of hearing at certain or all measured frequencies and the volume required for the perception of the respective tones may possibly already allow an estimate to be made in respect of the severity of the loss of hearing. Such hearing tests in respect of the threshold of hearing at different frequencies (pure-tone test) have already been offered for many years over the Internet and can therefore be carried out by interested parties on their own and in the comfort of their own home. A disadvantage is that this requires relatively precise calibration of the loudspeaker or headphones used by the test person.

A simple hand-held hearing-test instrument for carrying out a pure-tone hearing test has, for example, been disclosed in the published European patent application EP 1 813 190 A1, corresponding to U.S. patent publication No. 2007/0189545.

Furthermore, a multiplicity of hearing tests is known that allow a statement to be made in respect of the capability of a person for understanding speech. Reference is made here in an exemplary fashion to the intelligibility tests developed by the Hörzentrum Oldenburg (e.g. Oldenburger Sentence Test).

From time to time, simple intelligibility tests are also offered over the Internet, in which tests, for example, simple words (e.g. apple, ball, house, one, two, three, etc.) are read out and a test person is presented with the corresponding words or symbols for selection, for example on a display.

In addition to changing the volume of the presented acoustic signals, interference signals may likewise be superposed thereon during the presentation when the aforementioned hearing tests are carried out. In doing so, the signal-to-noise ratio (SNR) may also be varied when a corresponding hearing test is carried out. This is because many people who are hard of hearing find it particularly difficult to understand speech if there is simultaneous interference noise.

The article by Christian Lorenzi, Gaëtan Gilbert, Héloïse Carn, Stéphane Garnier, Brian C. J. Moore: entitled "Speech Perception Problems of the Hearing Impaired Reflect Inability to Use Temporal Fine Structure"; PNAS Dec. 5, 2006, vol. 103, no. 49, 18869 discloses an intelligibility test, in which the subjects should identify meaningless syllables, which for example are respectively composed of a vowel-consonant-vowel sequence. Inter alia, the syllables are also presented together with superposed, fluctuating interference noise.

SUMMARY OF THE INVENTION

It is accordingly an object of the invention to provide a hearing-test method which overcomes the above-mentioned disadvantages of the prior art methods of this general type, which can be carried out easily and automatically, and, more particularly, can also be carried out over the Internet.

With the foregoing and other objects in view there is provided, in accordance with the invention a method for testing hearing of a person. The method includes the steps of:
a) providing a hearing-test application on a network-accessible computer;
b) calling the hearing-test application by the person via a network by means of a personal computer of the person;
c) selecting and presenting an acoustic speech signal in a form of at least one meaningless syllable;
d) presenting the meaningless syllable and a number of additional meaningless syllables on a graphical user interface of the personal computer;
e) selecting, via the person, a heard meaningless syllable from displayed meaningless syllables;
f) evaluating a selection that was made; and
g) repeating the method steps c) to f) until an interrupt criterion is satisfied.

In order to carry out the hearing-test method according to the invention, a hearing-test application is advantageously provided on a computer that is accessible over a network, more particularly a computer network such as the Internet. The person (test person) can then set up a connection to the computer, for example over the Internet and/or a mobile radio network, and start the hearing-test application using a personal computer (PC, notebook, PDA, smartphone, etc.). Hence the hearing-test method can be carried out automatically at any time, and, more particularly, it can be carried out without the presence of a person skilled in the art, such as an ENT practitioner, audiologist, etc.

In order to assess if there is a hearing impairment, the presentation of speech signals provides a more reliable statement than pure-tone audiometry, in which merely sinusoidal tones are presented. So that the hearing test can be carried out internationally, more particularly language independently, without change, the presented speech signal preferably contains meaningless syllables, so-called logatomes. These can consist of e.g. vowel-consonant-vowel (aba, aca, ada, . . . ) or consonant-vowel-consonant (bab, beb, bib, . . . ) sequences. Optionally, these meaningless syllables should be checked and only those should be selected that do not make any sense in any important language. The presented syllables preferably result from speech recordings. However, they can also be generated synthetically.

A presented syllable (e.g. aba) is finally displayed on a test person's graphical user interface together with other syllables that have a similar sound (e.g. ada, aga, aha, aka, . . . ). The test person selects the syllable they thought they heard from the displayed syllables, for example by using a pointer instrument. Alternatively, the syllable identified by the test person can also be repeated by them and be registered by voice recognition.

Finally, there is an evaluation of the selection that was made. In the simplest case, this characterizes the selection as being right or wrong.

The test is repeated with a new selection of meaningless syllables until an interrupt criterion is satisfied.

In a preferred embodiment of the invention, an interference signal, more particularly noise, is superposed onto the presented speech signal. This is because the calibration of the personal computer of the test person is less important when speech signals are present in interference noise. Then the test signals only have to be presented at a volume at which they are easily perceptible. Hence, the hearing test is largely independent of the type and quality of the personal computer of the test person. The sensitivity of the hearing test emerges from a variation in the signal-to-noise ratio (SNR). In the process, the test initially starts with no noise component or a small noise component, and the noise component then successively increases relative to the speech component in each run-through until the test person no longer correctly identifies the speech signal. In one possible variant of the invention, the test is completed here and a result of the test is the lowest signal-to-noise ratio that was still identified correctly. In another variant, the test is repeated at least once at the signal-to-noise ratio at which the identification was incorrect for the first time in order to determine whether this is a reproducible test result. If need be, the test is subsequently continued at a lower SNR, or else it is completed if the repetition also leads to a negative result. Furthermore, one variant of the invention can optionally also recheck the lowest signal-to-noise ratio at which identification was without errors.

The ratio between speech signal and interference signal at which the test person no longer identifies the speech signal then permits a reliable statement to be made as to whether there is a hearing impairment. The assessment of whether there is a hearing impairment emerges, in particular, from a comparison of the result achieved by the test person with a typical value range for people with normal hearing. If the result achieved by the test person falls into this value range, they are classed as having "normal hearing". There preferably is automatic corresponding notification of the test person. If the value range of people with normal hearing could not be achieved, the test person is classed as "hard of hearing". Here too there preferably is corresponding notification of the test person, optionally with specifying further information, e.g. a possible classification of the hearing impairment (light, medium, severe), counseling options, etc.

A further improvement in the reliability or sensitivity of the hearing test can be achieved by virtue of the fact that fluctuating noise, more particularly amplitude-modulated noise with a preferably random modulation, is used as an interference signal. Using a modulated interference noise provides high sensitivity for a hearing impairment because, particularly in the case of inner ear hearing loss, the threshold in the case of modulated sounds is raised significantly with respect to people with normal hearing.

Particularly reliable and good results furthermore emerge if the speech signal is in each case presented in the region of a minimum of the fluctuating interference signal.

Other features which are considered as characteristic for the invention are set forth in the appended claims.

Although the invention is illustrated and described herein as embodied in a hearing-test method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a flowchart showing how to carrying out a hearing-test method according to the invention; and FIG. 2 is a graph showing how a hearing test is carried out in the case of a test person who is hard of hearing and a test person with normal hearing.

DETAILED DESCRIPTION OF THE INVENTION

Referring now to the figures of the drawing in detail and first, particularly, to FIG. 1 thereof, there is shown a flow chart for carrying out an exemplary hearing-test method. A hearing-test application for carrying out the method according to the invention is, in a first method step S1, provided on a computer that is accessible over a network, more particularly over the Internet.

In a second method step S2, a person (test person) sets up a connection between the computer, with the provided hearing-test application, and their personal computer (PC, notebook, PDA, smartphone, etc.), and initiates the hearing-test application, preferably by use of a graphical user interface. A keyboard and/or a computer mouse are preferably used for the operation. However, other control methods, e.g. speech control are also possible. The hearing test is preferably started by actuating a "start button".

Optionally, there now first of all is a query or a test in a further method step as to whether headphones are connected or a loudspeaker is switched on and whether the set volume is comfortable.

In the subsequent method step S3, there is the automatic selection and presentation of an acoustic speech signal in the form of a meaningless syllable from a multiplicity of possible meaningless syllables that, where possible, were preselected such that they can be used internationally (they have no meaning internationally).

In a method step S4, the presented syllable is displayed together with other, preferably similar, syllables on a graphical user interface of the personal computer of the test person. The syllables are preferably constructed in the form vowel-consonant-vowel and the similar presented syllables preferably only differ in terms of their consonant.

In the subsequent method step S5, the test person selects the displayed meaningless syllable they thought they heard from the displayed syllables, preferably by use of a pointer instrument (computer mouse) on the graphical user interface. Optionally, the buttons "repeat test" or "unintelligible" can also be offered for actuation.

Finally, in a subsequent method step S6, there is an automatic evaluation of the selection made by the test person. More particularly, it is registered whether the selection corresponds to the actually presented syllable. Furthermore, a decision is made in a method step S7 as to whether the test should be continued by selecting a new syllable by jumping to method step S3, or whether it should be completed in a method step S8. In particular, the test is completed if an interrupt criterion is satisfied, e.g. there is a clear result in respect of the hearing of the test person or there has been a certain number of run-throughs (e.g. 8). If the interrupt criterion has not been satisfied, the hearing test is continued in method step S3 and a syllable is again selected and presented.

In order to be able to make a statement relating to the hearing of the test person, an interference signal is superposed on the speech signal presented in method step S3. This interference signal can be a noise signal (e.g. white noise). The presented speech signal and/or the interference signal are then varied in each run-through of the test such that there is a change in the ratio of the signal levels between the speech signal and the interference signal (SNR).

A possible sequence of the variation of the mean signal level of the interference signal in the case of an unchanging signal level in the successively presented speech signals, and hence a variation in the signal-to-noise ratio (SNR), is shown in FIG. 2. The graph plots the progression of the test for both a test person with normal hearing (lower curve profile "B") and a test person who is hard of hearing (upper curve profile "A").

In the exemplary embodiment, the test starts with an SNR of approximately 0 dB, i.e. the mean signal levels of the speech signal and interference signal are approximately equal. If the test person correctly identifies the syllable presented thus, the subsequent test progresses as per the lower curve profile B. Here, the signal-to-noise ratio is reduced either by lowering the signal level of the speech signal, compared to the preceding test run-through, while the mean signal level of the noise signal remains constant or by keeping the signal level of successively presented speech signals constant and increasing the interference-signal level after each run-through. The signal-to-noise ratio is then reduced step-wise with each run-through until the test person no longer correctly identifies the last-spoken syllable. Then either the test is completed or—for checking purposes—the last reduction in the SNR is undone and a syllable is presented again in order to test whether the syllable is identified correctly again and hence the threshold of syllable recognition under the influence of interference noise was registered correctly.

If the test person does not correctly identify the first presented syllable, the subsequent test progresses e.g. as per the upper curve profile A in FIG. 2. Here the speech signal is increased step-wise with respect to the interference signal until the test person correctly identifies the last-spoken syllable. Here it is also possible to undo the last increase in the SNR for checking purposes in order to test precisely the threshold at which the presented syllables are reliably identified. In the exemplary embodiment as per FIG. 2, the hearing test is in each case automatically completed after 8 run-throughs.

In a preferred embodiment of the invention, the magnitude of the improvement or deterioration of the signal-to-noise ratio between two test run-throughs is variable. Here the test first of all starts off with relatively large steps until a syllable was, for the first time, no longer identified correctly or a syllable was, for the first time, identified correctly. Then there is a continuation around the value of the last-set SNR with smaller steps, as described above, in order to limit the threshold, at which the presented syllables are no longer reliably registered, as narrowly as possible.

The invention claimed is:

1. A method for testing hearing of a person, which comprises the steps of:
    a) providing a hearing-test application on a network-accessible computer;
    b) calling the hearing-test application by the person via a network by means of a personal computer of the person;
    c) selecting and presenting an acoustic speech signal in a form of at least one meaningless syllable and superposing a fluctuating interference signal onto the acoustic speech signal presented, the acoustic speech signal being presented in a region of a minimum of the fluctuating interference signal;
    d) presenting the meaningless syllable and a number of additional meaningless syllables on a graphical user interface of the personal computer;
    e) selecting, via the person, a heard meaningless syllable from displayed meaningless syllables;
    f) evaluating a selection that was made; and
    g) repeating the method steps c) to f) until an interrupt criterion is satisfied.

2. The method according to claim 1, wherein at least one of the acoustic speech signal or an interference signal is selected or presented for repeating the method steps c) to f), depending on an evaluation of the selection made by the person in respect of at least one previous run-through of method steps c) to f).

3. The method according to claim 2, which further comprises modifying a signal-to-noise ratio between the acoustic speech signal and the interference signal.

4. The method according to claim 3, which further comprises modifying the signal-to-noise ratio by levels with variable heights.

5. The method according to claim 1, wherein the fluctuating interference signal is a noise signal.

* * * * *